US009456904B2

(12) United States Patent
Landry et al.

(10) Patent No.: US 9,456,904 B2
(45) Date of Patent: Oct. 4, 2016

(54) FACET FIXATION DEVICE

(71) Applicant: SpineSmith Partners, L.P., Austin, TX (US)

(72) Inventors: Michael Landry, Austin, TX (US); Kevin Dunworth, Austin, TX (US)

(73) Assignee: SpineSmith Partners, L.P., Austin, TX (US)

(*) Notice: Subject to any disclaimer, the term of this patent is extended or adjusted under 35 U.S.C. 154(b) by 90 days.

(21) Appl. No.: 14/061,570

(22) Filed: Oct. 23, 2013

(65) Prior Publication Data
US 2014/0114418 A1  Apr. 24, 2014

Related U.S. Application Data

(60) Provisional application No. 61/717,513, filed on Oct. 23, 2012.

(51) Int. Cl.
*A61F 2/44* (2006.01)
*A61B 17/70* (2006.01)

(52) U.S. Cl.
CPC ......... *A61F 2/4455* (2013.01); *A61B 17/7064* (2013.01)

(58) Field of Classification Search
CPC .... A61F 2/4455; A61F 2/4405; A61F 2/447; A61F 2/4465; A61F 2/446; A61B 17/869; A61B 17/7064
USPC .................................. 606/247–249
See application file for complete search history.

(56) References Cited

U.S. PATENT DOCUMENTS

| 6,824,564 B2* | 11/2004 | Crozet ....................... 623/17.11 |
| 7,291,170 B2* | 11/2007 | Huppert ..................... 623/17.11 |
| 8,900,310 B2* | 12/2014 | Carlson et al. ............. 623/17.16 |
| 2004/0082953 A1* | 4/2004 | Petit ............................... 606/61 |
| 2005/0143733 A1* | 6/2005 | Petit ............................... 606/60 |
| 2008/0255666 A1* | 10/2008 | Fisher et al. ............... 623/17.16 |
| 2009/0306671 A1* | 12/2009 | McCormack et al. .......... 606/90 |
| 2010/0331895 A1* | 12/2010 | Linke ............................ 606/304 |
| 2011/0166660 A1* | 7/2011 | Laurence ................... 623/17.16 |

* cited by examiner

*Primary Examiner* — Kevin T Truong
*Assistant Examiner* — Si Ming Ku
(74) *Attorney, Agent, or Firm* — Winstead PC

(57) ABSTRACT

The invention features an implant assembly for stabilization of a facet joint including an implant having a U-shaped body. The U-shaped body has a rounded front end, an open back end, first and second elongated components extending from the rounded front end, forming the U-shaped body and ending at the open back end and a helical structure extending within the U-shaped body that serves as a locking mechanism.

17 Claims, 4 Drawing Sheets

FACET FIXATION DEVICE

CROSS-REFERENCES TO RELATED APPLICATIONS

This Application claims the benefit under 35 U.S.C. §119(e) of U.S. Provisional Patent Application No. 61/717,513 filed Oct. 23, 2012 which is incorporated herein by reference in its entirety as if fully set forth herein.

BACKGROUND OF THE INVENTION

The human lumbar spine includes individual vertebras that are connected to each other via a three joint complex—the vertebral disc and two facet joints. Under normal circumstances these structures function to protect the neural structures and to allow us to stand erect, bear axial loads, and be flexible for bending and rotation. When disorders of the spine occur due to disease or trauma, one or more of these spinal structures may function abnormally resulting in pain. In these pathologic circumstances, surgery may be required to stabilize the spine, protect the neural structures, and to relieve patient discomfort. Spinal fusion works well because it stops pain due to movement at the facet joints and intervertebral discs, holds the spine in place after correcting deformity, and prevents instability and or deformity of the spine after spine procedures such as discectomies, laminectomies or corpectomies.

The use of posterior stabilization rods and pedicle screws in combination with the insertion of an intervertebral implant is an effective method of spinal fusion. However, the operating procedure for implanting pedicle screws and rods is very invasive, and can result in many different postoperative problems. Accordingly, it is desirable to provide alternatives to pedicle screws and rods that provide stabilization to augment the intervertebral procedure.

SUMMARY OF THE INVENTION

The invention features an implant assembly for stabilization of a facet joint including an implant having a U-shaped body. The U-shaped body comprises a rounded front end, an open back end, first and second elongated components extending from the rounded front end, forming the U-shaped body and ending at the open back end and a helical structure extending within the U-shaped body that serves as a locking mechanism.

DETAILED DESCRIPTION OF EXEMPLARY EMBODIMENTS

Figure 1A:
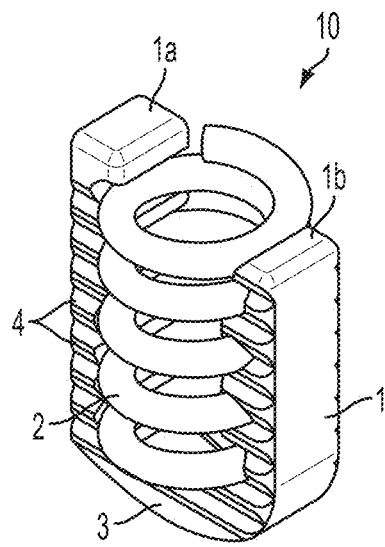
FIG. 1A shows a perspective view of an implant assembly in accordance of an embodiment of the invention.

An embodiment of the invention is directed to an implant assembly for stabilization of a spinal facet joint including an implant having a U-shaped body wherein the U-shaped body comprises a rounded front end, an open back end, first and second elongated components extending from the rounded front end, forming the U-shaped body and ending at the open back end and a helical structure extending within the U-shaped body that serves as a locking mechanism. In certain embodiments of the invention, grooves or threads are introduced in the first and second elongated components.

In embodiments of the invention, the helical structure locks the U-shaped body in place within a joint. In certain embodiments of the invention, the insertion of the U-shaped body generally distracts the facet joint. Biologically active materials meant to promote fusion (i.e. stem cells, bone void filler, etc.) can be inserted into the space created by the insertion of the implant assembly.

In certain embodiments of the invention, the assembly comprises bilateral placement of two sets of implants. In certain aspects of the invention, the assembly is used in conjunction with an intervertebral implant.

An embodiment of the invention allows the soft tissues in the facet joint to be removed and the facet joint to be treated with stem cells, synthetic bone substitute, BMP or any other biologically active substance which promotes fusion. This is enabled by a U-shaped body. The U-shaped body, when placed in the joint space, expands the joint space and creates the necessary space to remove the native soft tissues.

In certain embodiments of the invention, grooves and/or threads are introduced in the first and second elongated components to secure the implant in place.

In other embodiments of the invention, in place of grooves or threads in the first and second elongated components, a helical structure is introduced into the open part of the U-shaped body. The helical structure anchors the U-shaped body to the bone.

In certain embodiments of the invention, the U-shaped body/spacer is open on one end. This allows the surgeon to work on the joint space after the spacer is placed and with the joint distracted. This extra space will allow the surgeon to used reamers, rasps, drills, rongures, files, etc. to remove more soft tissue from the joint. The ability to remove residual soft tissue from joints being fused is advantageous because these tissues can lead to non-unions and pseudoarthrosis.

In other embodiments of the invention, after the joint space is prepared, the surgeon implants the helical anchor which locks the spacer in place to prevent migration. This is accomplished while minimizing the volume of the anchor by using a helical shape instead of a fenestrated screw. The helical anchor is self-locking as the final turn is made In certain embodiments of the invention, either before, during or after the implantation of the helical anchor within the U-shaped body, biologically active materials meant to promote fusion (i.e. stem cells, bone void filler, etc.) can be inserted into the space within the helical anchor. Contact between the inserted material and native bone is maximized by the helical nature of the anchor, because of its low volume and open structure.

An embodiment of the invention is directed to a lumbar facet fixation device intended to be used in conjunction with an anterior fusion. When implanted bilaterally, the facet fixation device described should provide supplementation stabilization to the spine while a biological fusion matures in the interbody space and the two associated facet joints at that level. The device is installed in such a way that the facet joint is easily prepared to accept a biologically active material that will promote bone fusion in the joint. Additionally, the device has a largely open structure relative to the bone proximate the facet joint which will allow for a relatively large volume of biologically active material to be placed and for the resultant mature bone fusion mass to be well connected to the native tissues.

In embodiments of the invention, the implant assembly is comprised of two components: a U-shaped spacer and a helical bone anchor. FIGS. 1A to 1D and FIGS. 2A to 2B show standard and isometric views of the implant assembly of the claimed invention. Looking at FIG. 1A, the implant assembly 10 comprising a U-shaped spacer 1 is shown. The U-shaped spacer 1 is not necessarily symmetric about any plane. As shown in FIG. 1A, one arm 1a is longer than the other 1b. In certain embodiments of the invention, the bottom of the U-shaped spacer 3 is angled. The purpose of the variation in sizes of the arms of the spacer and the angled shaped of the bottom of the spacer is to allow the U-shaped spacer to accommodate the shape of the facet joint in which it is inserted, and the several shapes and sizes that would be necessary to accommodate various patient anatomy and spinal levels.

Figure 3:
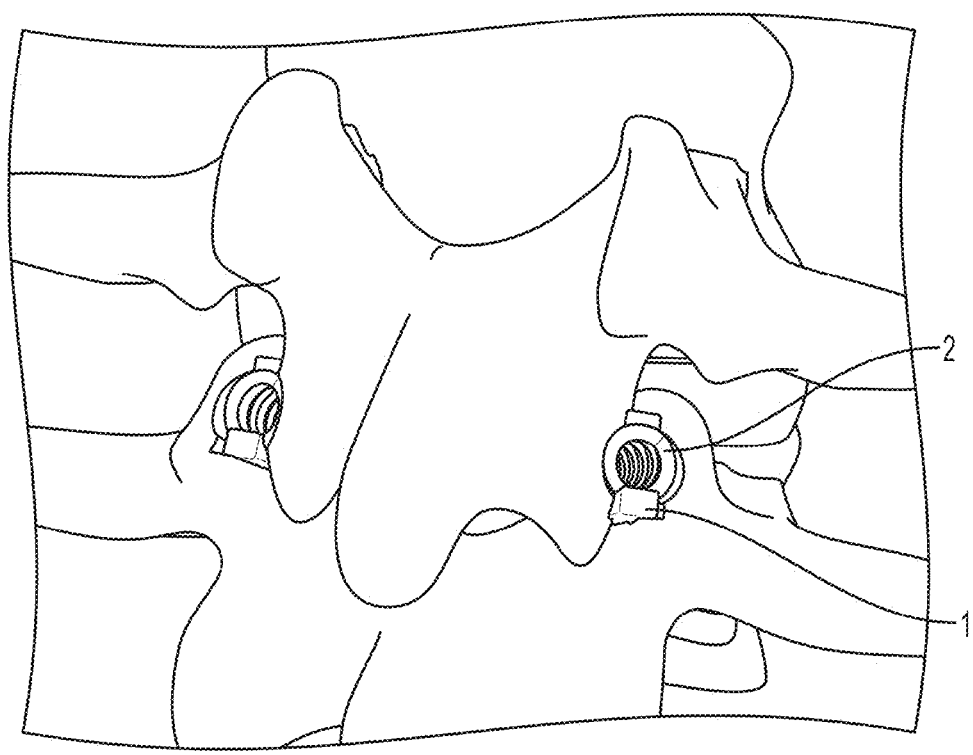
FIGS. 3 and 4 show the placement of an implant assembly in a facet joint in accordance with an embodiment of the invention.
Figure 4:
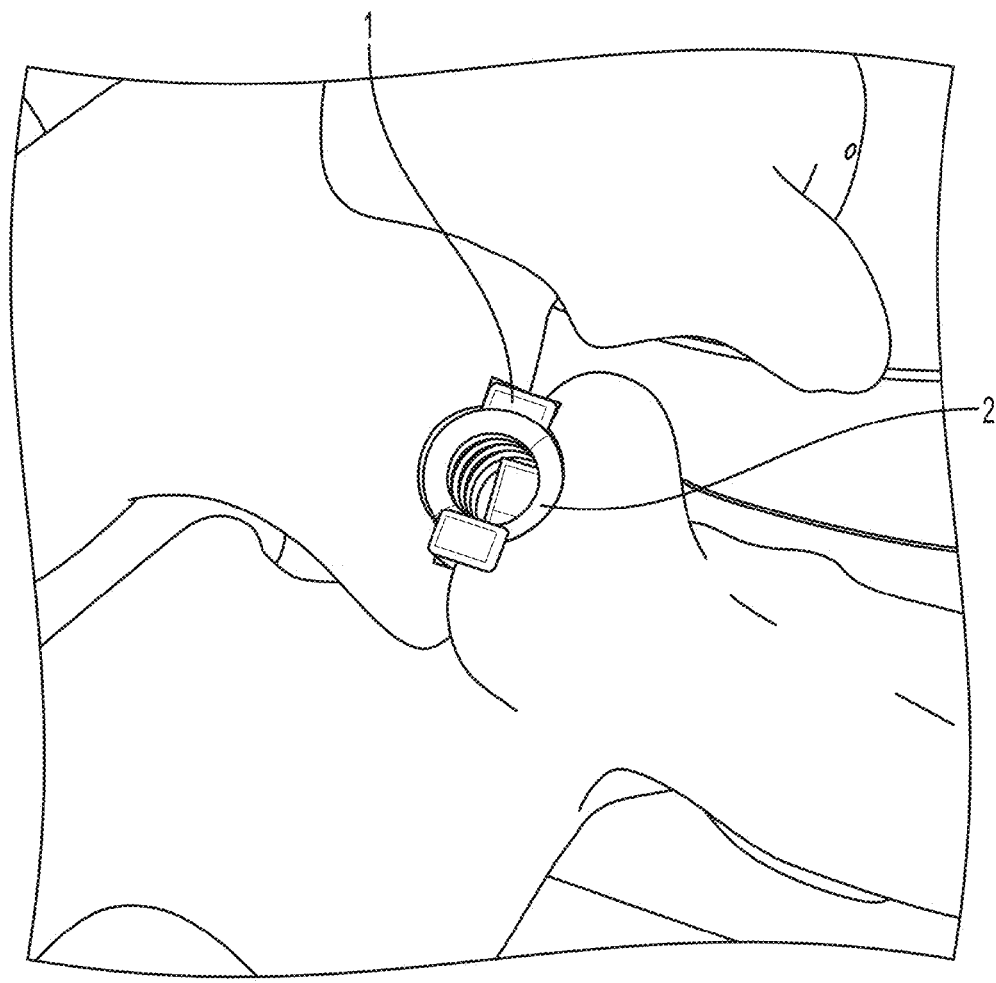

Continuing to look at FIG. 1A, a helical anchor 2 is inserted into the U-shaped spacer 1. In certain embodiments of the invention, the helical anchor 2 is similar in shape to a compression spring. In certain embodiments of the invention, the arms of the U-shaped spacer comprise grooves 4 on both faces of the arms as shown in FIG. 1A. The grooves 4 increase friction between the spacer 1 and the bone when the implant assembly 10 is placed within a joint of a subject (as shown in FIGS. 3 and 4).

Figure 1B:
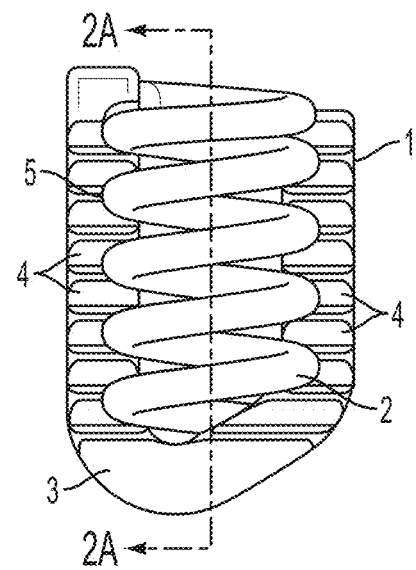
FIG. 1B shows a side view of an implant assembly in accordance of an embodiment of the invention.

In certain embodiments of the invention, the U-shaped spacer 1 comprises indentations 5, which are shaped to accommodate the helical anchor 5. As shown in FIG. 1B, the indentations 5 interact with the helical anchor 2 and accommodate the portions of the helical anchor that contact the inner face of the U-shaped spacer 1. In certain embodiments of the invention, the indentations 5 are configured to position the helical anchor 2 within the U-shaped spacer. In other embodiments of the invention, the indentations 5 capture the helix at each of the indentations 5.

Figure 1C:
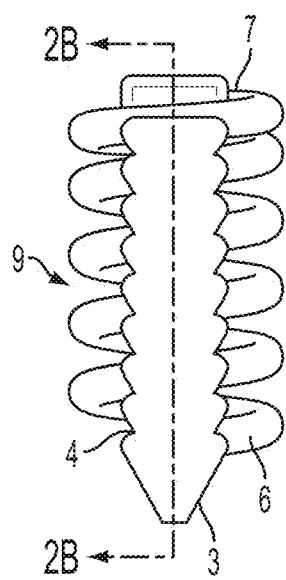
FIG. 1C shows a side view of an implant assembly in accordance of an embodiment of the invention.

The leading edge 6 and trailing edge 7 of the helical anchor 2 are shown in FIG. 1C. In certain embodiments of the invention, the pitch of the leading edge 6 is unchanged. The leading edge 6 is shaped into a point to facilitate the insertion of the implant assembly 10 into a joint. The trailing edge 7 has a variable pitch. The purpose of the variable pitch for the trailing edge 7 is to provide a locking mechanism for the helical anchor 2 within the implant assembly 10. During the assembly of the implant 10, when the helical anchor is inserted into the U-shaped spacer 1, as the final turn of the helical anchor 2 is made into the U-shaped spacer 1, the pitch is reduced, which causes the trailing edge 7 to snap into place where it contacts an arm of the U-shaped spacer 1. This locks the helical anchor 2 into place within the U-shaped spacer 1 and prevents the helical anchor 2 from reversing out of the spacer 1. In addition to the locking mechanism, the variable pitch feature of the trailing edge 7 provides a surgeon with tactile feedback indicating that the anchor 2 is fully inserted into the spacer 1.

Figure 1D:
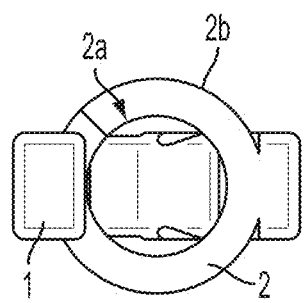
FIG. 1D shows a top view of an implant assembly in accordance of an embodiment of the invention.

As set forth in FIG. 1D, an internal space 2a is formed within the helical anchor. The internal space 2a is bounded by the helical anchor 2 and the sides and bottom of the U-shaped spacer 1. The internal space 2a is typically filled with biologically active material that is meant to promote fusion i.e. stem cells, bone void filler, etc. The outer edge 2b of the helical anchor contacts the bone within a joint and anchors the U-shaped spacer 1 to the bone and prevents the migration of the implant assembly 10 after it has been inserted into a facet joint.

Figure 2A:
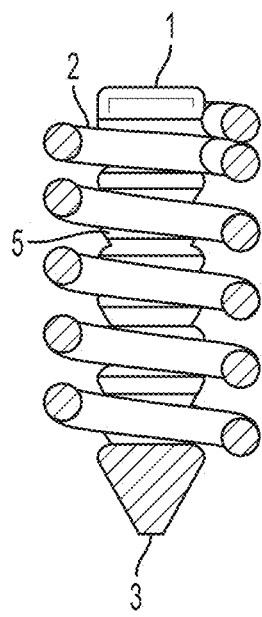
FIGS. 2A and 2B show a cross-section view of an implant assembly in accordance of an embodiment of the invention.
Figure 2B:
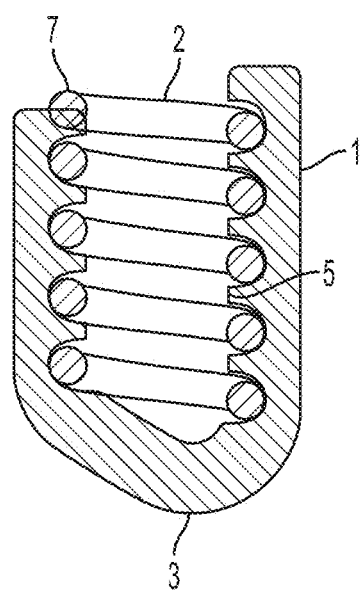

FIG. 2A shows a representation of a cross-section 2A-2A as set forth in FIG. 1B. FIG. 2A shows the coils of the helical anchor 2 housed within the indentations 5 of the U-shaped spacer 1. FIG. 2B shows a representation of a cross-section 2B-2B as set forth in FIG. 1C. FIG. 2B shows the coils of the helical anchor 2 housed within the indentations 5 of the U-shaped spacer 1 and the locked position of the trailing edge 7 where it contacts an arm of the U-shaped spacer 1.

FIG. 3 illustrates two assembled implants implanted bilaterally in the facet joint of the lumbar spine. FIG. 4 shows a close-up view of one of implants from FIG. 3.

An embodiment of the invention provides a surgical procedure using the implant assembly of the claimed invention. First, a facet joint is targeted with a k-wire using the trajectory from an lateral to medial, superior to inferior approach such that the k-wire enters between the inferior articular surface of the superior vertebra and the superior articular process of the inferior vertebra. A series of dialators is used over the initial k-wire to split the muscle and blunt dissect to the facet joint. All but the largest dilator and the k-wire are removed. A cannulated drill is used to drill over the k-wire to the anterior aspect of the facet joint. The drill has an outer diameter that is slightly larger than the internal diameter of the helical anchor. A box chissel is used to prepare the joint for the spacer by making a rectangular cut slightly larger than the spacer into the joint.

The U-Shape spacer in inserted in the correct orientation, usually angled bottom end (3) first, based on the shape of the facet and the shape of the implant. Trials may be used to determine the proper shape and height for the facet joint. The correct size will fill the joint and distract the joint to provide ligamentous tension on the spacer to stabilize the spine and spacer. Standard instruments are used to clear all tissues that remain in the joint inside the U-Shape of the spacer. Using a custom inserter, the helical anchor is inserted by rotating it into the U-shaped spacer until the end of the anchor snaps below either arm (1a or 1b) of the spacer, preventing the anchor from reversing out of the bone.

The space inside the U-shaped spacer and inside the helical anchor is filled with a biologically active material designed to promote bone fusion, or a combination of materials. A packing tool is used to compress the material and generate contact with the native bone. If necessary, the implant construct can be capped with a component designed to retain the material and prevent its movements while maturation occurs. This can be integrated into the helical anchor, spacer or a separate component. If necessary, the procedure can be repeated on another area of the spinal unit.

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:

1. An implant assembly for stabilization of a spinal facet joint including an implant having a U-shaped body wherein the U-shaped body comprises a rounded front end, an open back end, a first elongated component, a second elongated component, the first elongated component and the second elongated component extending from the rounded front end forming the U-shaped body and ending at the open back end, and a helical structure extending within the U-shaped body;

wherein a length of the first elongated component is greater than a length of the second elongated component; and wherein the helical structure comprises a coiled wire.

2. The implant assembly of claim 1, wherein grooves or threads are introduced in the first elongated component and the second elongated component.

3. The implant assembly of claim 1, wherein the helical structure locks the U-shaped body in place within a joint.

4. The implant assembly of claim 1, wherein insertion of the U-shaped body distracts the facet joint.

5. The implant assembly of claim 4, wherein biologically active materials meant to promote fusion can be inserted into a space created by the insertion of the implant assembly.

6. The implant assembly of claim 1, wherein the assembly comprises bilateral placement of two devices.

7. The implant assembly of claim 1, wherein the assembly is used in conjunction with an additional intervertebral implant.

8. The implant assembly of claim 1, wherein the helical structure comprises a unitary helical anchor, the unitary helical anchor comprising a leading edge with a first pitch and a trailing edge with a second pitch that locks the helical structure within the U-shaped body when the trailing edge is inserted into the U-shaped body.

9. The implant assembly of claim 1, wherein the rounded front extends to a single apex that is offset from a centerline formed between the first elongated component and the second elongated component.

10. An implant assembly for stabilization of a spinal facet joint including an implant having a U-shaped body wherein the U-shaped body comprises a rounded front end, an open back end, a first elongated component, a second elongated component, the first elongated component and the second elongated component extending from the rounded front end forming the U-shaped body and ending at the open back end, and a helical structure extending within the U-shaped body;

wherein the rounded front extends to a single apex that is offset from a centerline formed between the first elongated component and the second elongated component; and wherein the helical structure comprises a compressible coiled wire that forms an internal bore through the helical structure, the coiled wire comprising:

a leading edge with a first pitch, the first pitch corresponding to a pitch of the U-shaped body;

a trailing edge with a second pitch that is different than the first pitch and the pitch of the U-shaped body; and wherein, upon insertion of the helical structure into the U-shaped body, the second pitch locks the helical structure within the U-shaped body by deforming the coiled wire.

11. The implant assembly of claim 10, wherein grooves or threads are introduced in the first elongated component and the second elongated component.

12. The implant assembly of claim 10, wherein the helical structure locks the U-shaped body in place within a joint.

13. The implant assembly of claim 10, wherein insertion of the U-shaped body distracts the facet joint.

14. The implant assembly of claim 13, wherein biologically active materials meant to promote fusion can be inserted into a space created by the insertion of the implant assembly.

15. The implant assembly of claim 10, wherein the assembly comprises bilateral placement of two devices.

16. The implant assembly of claim 10, wherein the assembly is used in conjunction with an additional intervertebral implant.

17. The implant assembly of claim 10, wherein a length of the first elongated component is greater than a length of the second elongated component.

* * * * *